US006899676B1

(12) United States Patent
Stegmann

(10) Patent No.: US 6,899,676 B1
(45) Date of Patent: May 31, 2005

(54) METHOD FOR DETERMINING THE STRESS CAPACITY OF A PERSON

(76) Inventor: Heiner Stegmann, Friedrich-Ebert-Anlage 25, 63450 Hanau (DE)

(*) Notice: Subject to any disclaimer, the term of this patent is extended or adjusted under 35 U.S.C. 154(b) by 0 days.

(21) Appl. No.: 09/926,129
(22) PCT Filed: Mar. 8, 2000
(86) PCT No.: PCT/EP00/02030
§ 371 (c)(1),
(2), (4) Date: Dec. 7, 2001
(87) PCT Pub. No.: WO00/53091
PCT Pub. Date: Sep. 14, 2000

(30) Foreign Application Priority Data

Mar. 8, 1999 (DE) .......................................... 199 09 852

(51) Int. Cl.[7] .................................................. A61B 5/00
(52) U.S. Cl. ........................ 600/300; 128/898; 128/920
(58) Field of Search ................................. 600/300, 529, 600/532, 531; 128/897, 898, 920, 923; 702/19

(56) References Cited

U.S. PATENT DOCUMENTS

| 4,622,980 A | * | 11/1986 | Kunig ........................ 600/520 |
| 5,782,772 A | * | 7/1998 | Stegmann ................... 600/529 |
| 6,387,053 B1 | * | 5/2002 | Pessenhofer ............... 600/531 |

OTHER PUBLICATIONS

Prusaczyk, WK, et al., "A computational method for determination of the individual anaerobic threshold," Computers in Biology and Medicine, vol. 23, No. 4, pp. 327–331, 1993.*

Baldari C, et al., "A simple method for individual anaerobic threshold as predictor of max lactate steady state", Medicine and Science in Sports and Exercise, vol. 32, No. 10, pp. 1798–1802, 2000.*

* cited by examiner

Primary Examiner—Eric F. Winakur
(74) Attorney, Agent, or Firm—Dennison, Schultz, Dougherty & MacDonald

(57) ABSTRACT

The invention relates to a method for determining the stress capacity of a person taking into consideration the individual anaerobic threshold by measuring lactate concentrations in relation to physical effort. To make it possible to deduce from the changes in lactate concentration other performance data characteristic of the person tested, the invention provides for the following process steps: measurement of time-dependent lactate concentration changes above the individual anaerobic threshold; adjustment of the measurement cure, in which lactate concentration is recorded in relation to time, to the measurement values obtained in this way; determination of a first rise in the measurement curve at a time $t_{IAT}$ which corresponds to the individual anaerobic threshold: determination of at least one other rise in the measurement curve at a time $t_x$ where $t_x > t_{IAT}$ and subtraction of the second rise from the first rise to determine a difference $\Delta A$.

4 Claims, 3 Drawing Sheets

METHOD FOR DETERMINING THE STRESS CAPACITY OF A PERSON

The invention concerns a process for determining the stress capacity of a person while taking into consideration the individual anaerobic threshold by measuring lactate concentrations in dependence upon the effort.

The lactate concentration of the blood plasma is predominantly determined in the stress capacity phase by the lactate influx, that is, by the predominantly diffusive lactate flow from the muscles into the blood plasma. This influx is driven by the concentration drop occurring between the muscle tissue, which produces the lactate, and the blood plasma. In the phase after the application of stress, instead, the influence of the lactate efflux, that is, the lactate elimination from the blood plasma is prevalent.

From the lactate concentration can be determined the so-called individual anaerobic threshold, which is a fixed, clearly reproducible value. The "individual anaerobic threshold" therein is also important for physiological parameters such as the evaluation of the physical effort, the blood pressure under stress, and coronary heart diseases.

Usually, the carried out the individual anaerobic threshold is undertaken via the determination of the lactic acid in the blood, wherein the changes of the lactic acid fraction are measured in dependence upon the work performed per time unit.

BACKGROUND OF THE INVENTION

In the literature, the determination of the individual anaerobic threshold according to Stegmann et al (Int. J. Sports Medicine 2 (1981), 160–165) has prevailed for the physiologic capacity diagnostic and has found wide applications. The individual anaerobic threshold determination according to Stegmann differs from other lactate threshold concepts in the consideration of the plasma lactate level in the phases during and after the application of stress. In the phase after the application of stress, the influence of the lactate efflux, that is, the lactate elimination from the blood plasma, is prevalent. The measurement of the lactate kinetic beyond the end of the stress and the use of this kinetic in the derivation of the individual anaerobic threshold presents the danger that, during the determination of the individual anaerobic thresholds, the parameters of the lactate influx as well as also the lactate efflux characteristic of the person being under stress must also be taken into consideration. From this consideration is derived a great advantage of the Stegmann threshold, since the determination of the individual anaerobic thresholds can be carried out continuously during the stress test at any desired set stages.

The individual anaerobic threshold according to Stegmann, however, can be determined not only via the continuous measurement of the lactate in the blood of a person, but also from the respiratory measured values of the per minute breathing volume, the 0 content of the per minute breathing volume, as well as the $CO_2$ content of the per minute breathing volume (European patent publication 0,742,693 B1).

SUMMARY OF THE INVENTION

The object of the invention is to further develop a process of the initially described kind, which provides the possibility of obtaining other characteristic performance data of a person from the lactate concentration changes.

According to the invention, the object is attained via the process steps of measuring the time-dependent lactate concentration changes above the individual anaerobic threshold, adjusting a measured curve to the obtained measured values in which the lactate concentration is recorded with respect to time, determining a first rise in the measured curve in one of the individual anaerobic thresholds according to time point $t_{IAT}$, determining at least one more rise in the measured curve at a time point $t_x$, with $t_x > t_{IAT}$, and subtracting the second rise from the first rise for determining a difference $\Delta A$.

Accordingly, stored curves or differences $\Delta A$ obtained from these can be compared with values obtained at other times on the same person or with measured curves of different persons or with standard values to obtain in this way characteristic data of the effort. The measured curves themselves can be recorded during a staged or continuous increase of the stress on the person.

According to the invention, the knowledge is used that, during the stress increase above the individual anaerobic threshold (IAT), a strong rise in the lactate concentration in the blood plasma takes place, since lactate accumulates by the predominance of the lactate influx with respect to the lactate efflux in the plasma compartment. If the rise in the lactate concentration time curve, which can also be called lactate accumulation rate, is characterized by the condition of an organism when reaching the individual anaerobic threshold (IAT), wherein a constant stress with the effort corresponding to the individual anaerobic threshold does not lead to a growing rise but to a suspension in the lactate concentration time curve at maximum levels, then, when the performance corresponding tol the individual anaerobic threshold is exceeded, a rapid rise in the lactate concentration in the blood plasma can be detected.

According to the, invention, a standardization of the lactate accumulation rate to that of the individual anaerobic threshold takes place, with the consequence that the characteristic performance values of the person are available.

BRIEF DESCRIPTION OF THE DRAWINGS

Other details, advantages, and features of the invention result, not only from the claims and the features which can be found therein—individually and/or in combination—but also from the following description of the figures.

In the figures.

DESCRIPTION OF THE PREFERRED EMBODIMENTS

Figure 5:
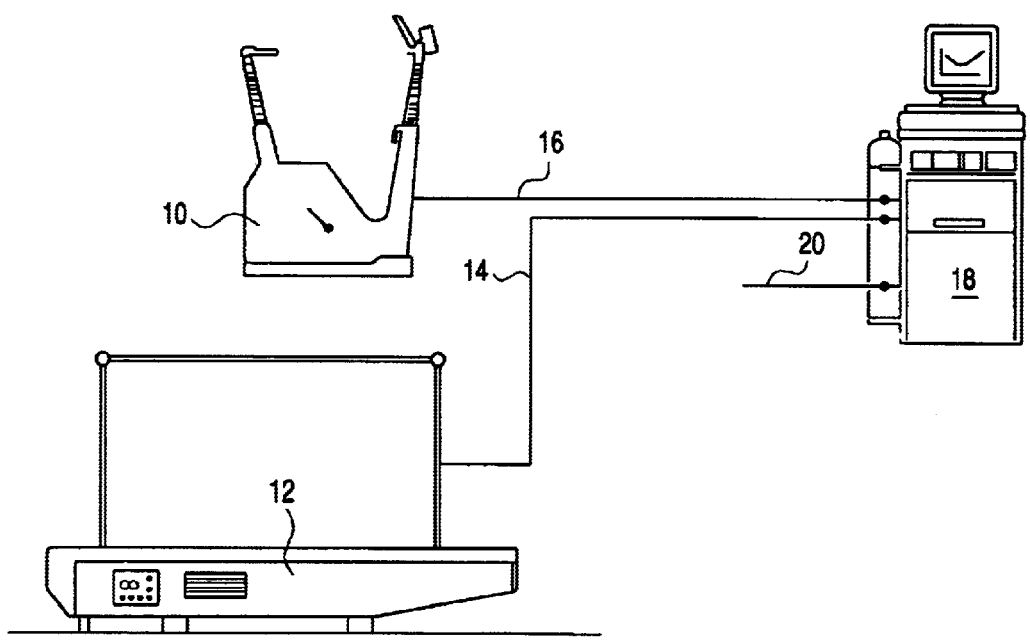
FIG. 5 shows a supply arrangement for determining lactate accumulation rates.

To obtain characteristic reproducible values about the effort or stress capacity of a person, the change of lactate concentration is measured in dependence upon the time stress. To measure the stress, as shown in FIG. 5, can be used a bicycle ergometer 10 or, for example, a treadmill 12 or another apparatus, or an arrangement, which can also be used for determining the individual anaerobic threshold (IAT). The apparatuses 10, 12 are connected via lines 14, 16 with the data processing device 18 to determine in this way the work performed per time unit. Furthermore, a time-dependent test of the blood of the person takes place. The corresponding values, that is, the characteristic values of the lactate concentration such as the lactic acid fraction are also supplied to the data processing device 18 (line 20).

Figure 1:
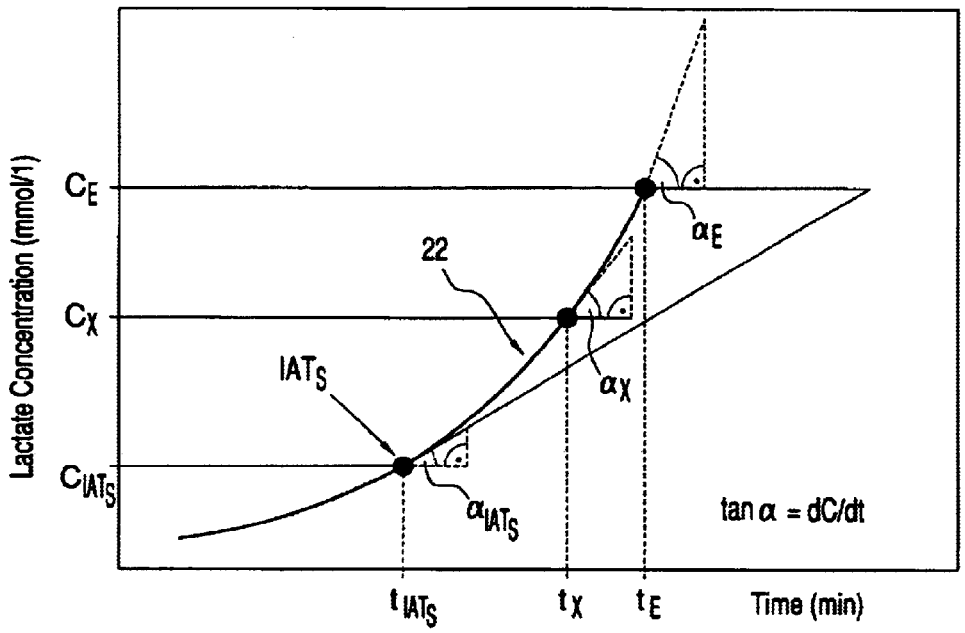
FIG. 1 shows a lactate performance curve.

From the values obtained in this way, the data processing 18 computes a measured curve in which, corresponding to FIG. 1, the concentration C of the lactate is recorded in mmol with respect to the time t, which is preferably recorded in minutes. The corresponding measured curve is provided in FIG. 1 with the reference numeral 22.

Figure 2:
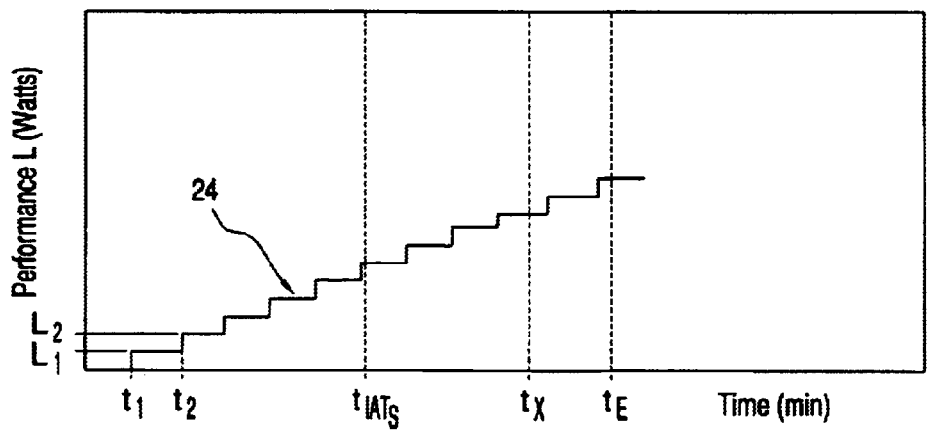
FIG. 2 shows a performance time curve with staged performance change assigned to the lactate performance curve according to FIG. 1.
Figure 3:
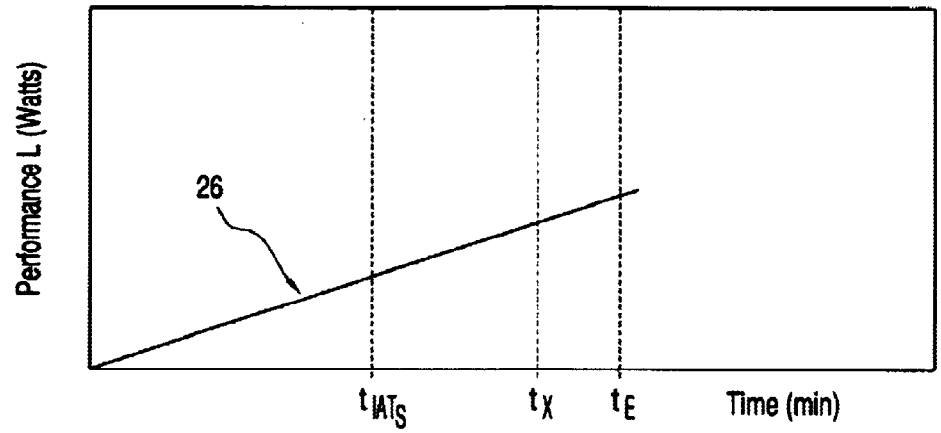
FIG. 3 shows a performance time curve with continuous performance change assigned to the lactate performance curve according to FIG. 1.

As can be seen in FIGS. 2 and 3, the stress increase can take placed in a staged or continuous manner (curve 26). Insofar, reference is made however to sufficiently known measuring processes.

The concentration change of the lactate is determined according to the invention not only up to the anaerobic individual threshold IAT, also above the constant stress limit, but also with a greater stress, wherein a rapid rise in the lactate concentration in the blood plasma can be detected. Also with the greatest stress takes place a staged (FIG. 2) or continuous stress increase (FIG. 3), that is, in a similar manner as is known from the determination of the individual threshold IAT. From the measured curve 22 are then determined the rises of the lactate concentration time curve at the time point $t_{IAT}$ corresponding to the individual anaerobic threshold IAT as well as also at other time points such as $t_x > t_{IAT}$ and, if necessary, up to the stress end $t_E$.

The corresponding rises can be considered as the lactate accumulation rate, wherein it can be recognized that the lactate accumulation rates clearly rise above the time point $t_{IAT}$, that is, the rise tan $\alpha_{IAT}$ at a time point $t_{IAT}$ is less than the rise tan $\alpha_x$ at a time point $t_x > t_{IAT}$, which is again smaller than the rise at a time point $t_E$ at the end of the stress.

From the lactate performance curve 22 above the individual anaerobic threshold IAT can then be obtained characteristic reproducible values of the stressed person, when an adjustment of the lactate accumulation rate takes place to that of the individual anaerobic threshold, that is, the difference $\Delta A$ between the rise tan $\alpha_x$ and the rise tan $\alpha_{IAT}$ is formed. This difference is a measure of the system disorder of the lactate concentration above the continuous stress corresponding to the individual anaerobic threshold and is therefore individually characteristic for each person.

The effort or stress capacity of a person can also be taken from the lactate performance curve which can be seen in FIG. 1 as well as also from a characteristic line 28, wherein the change of the lactate accumulation rate $\Delta A$ with respect to the performance L is recorded. The characteristic line 28 can be compared to a standard curve 30, a curve of the same person recorded at another time point, or the measured curve of another person, to derive in this way evidence about the effort or stress capacity and, if necessary, standard values.

Figure 4:
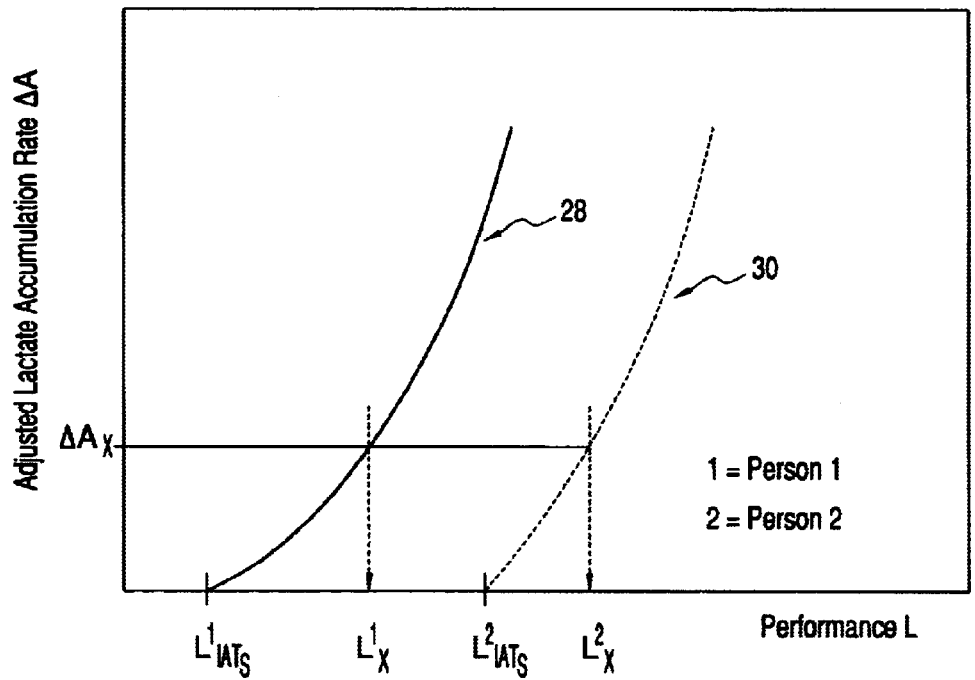
FIG. 4 shows the lactate accumulation rate changes in dependence upon the performance.

In FIG. 4 can be seen the correlation between different performances $L^1_x$ and $L^2_x$, which are obtained with equal lactate accumulation rate $\Delta A$ adjusted to the individual aerobic threshold in the destressing test.

In this way, a conclusion as to the destressing duration of a person results during the stress test from the determination of the lactate accumulation $\Delta A$ adjusted to the individual anaerobic threshold. This again means that the adjusted lactate accumulation rate $\Delta A$ can be used as a parameter for general training control. Also, the lactate accumulation rates $\Delta A$ adjusted to the individual anaerobic threshold can be evaluated with the purpose of detecting coronary heart diseases or evaluating blood pressure regulation processes.

What is claimed is:

1. Process for determining the stress capacity of a person while taking into consideration the individual anaerobic threshold by measuring lactate concentrations in dependence upon work performed, comprising the steps of measuring the time-dependent lactate concentration changes above the individual anaerobic threshold, plotting a curve of the measured values of the lactate concentration with respect to time, determining a first slope of the curve at time point $t_{IAT}$, at the individual anaerobic threshold, determining at least one more slope of the measured curve at a time point $t_x$, with $t_x > t_{IAT}$, and subtracting the second slope from the first slope for determining a difference $\Delta A$.

2. Process according to claim 1, wherein differences $\Delta A_x$ with x=1, 2 . . . are recorded with respect to the effort expended and the measured curves formed in this way are compared with standard curves, measured curves of different persons, or measured curves of the same person at different stress times.

3. Process according to claim 1, wherein the curves are measured during a staged effort change of the person.

4. Process according to claim 1, wherein the curves are measured during a continuous effort change of the person.

* * * * *